United States Patent
Boeglin et al.

[11] Patent Number: 6,046,335
[45] Date of Patent: Apr. 4, 2000

[54] HETEROCYCLIC COMPOUNDS

[75] Inventors: Patrick Boeglin, Rixheim, France;
Bansi Lal Kaul, Biel-Benken, Switzerland; Bruno Piastra, Huningue, France

[73] Assignee: Clariant BVI, Tortola, Virgin Islands (Br.)

[21] Appl. No.: 09/175,087

[22] Filed: Oct. 19, 1998

[51] Int. Cl.$^7$ ............................ C07D 471/16; C08K 34/95
[52] U.S. Cl. .................................. 546/32; 546/41; 524/82; 524/90; 106/31.77
[58] Field of Search ........................... 546/32, 41; 524/82, 524/90; 106/31.77

[56] References Cited

U.S. PATENT DOCUMENTS 5,510,403  4/1996  Kaul .......................................... 524/90

FOREIGN PATENT DOCUMENTS 561763    5/1975   Switzerland .
1488981  10/1977   United Kingdom .

OTHER PUBLICATIONS

European Search Report, Feb. 1999.

Derwent Abstract—DD 211456, Jul. 11, 1984.

Derwent Abstract—CH 561763, May 15, 1975.

Derwent Abstract—DE 2451049 (See C Above), Apr. 29, 1976.

Derwent Abstract—FR 2620713 (See A Above), Mar. 24, 1989.

*Primary Examiner*—Fiona T. Powers
*Attorney, Agent, or Firm*—Scott Hanf

[57] ABSTRACT

Compounds of the formula (I)

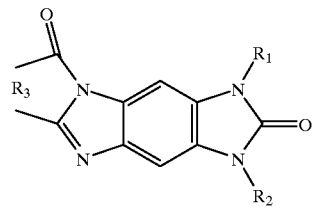

in which
$R_1$ and $R_2$ are identical or different and are hydrogen, $C_1$–$C_6$-alkyl, $C_6$–$C_{10}$-aryl, $(C_6$–$C_{10})$-aryl-$(C_1$–$C_6)$-alkyl or $(C_1$–$C_6)$-alkyl-$(C_6$–$C_{10})$-aryl, it being possible for the alkyl and/or aryl radicals to be substituted by hydroxyl, $C_1$–$C_6$-alkoxy, $C_6$–$C_{10}$-aryloxy or halogen, with the proviso that $R_1$ and $R_2$ are not simultaneously hydrogen, $R_3$ is a radical of the formula (II) or (III)

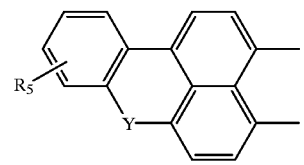

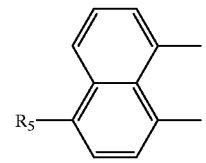

in which Y and $R_5$ are as defined in the description, are valuable colorants for the mass coloring of polymers, in electrophotographic toners and developers, in powder coating materials and in ink-jet inks.

10 Claims, No Drawings

HETEROCYCLIC COMPOUNDS

BACKGROUND OF THE INVENTION

FR-A-2620713 discloses a process for coloring polyamides with heterocyclic compounds which are described as pigments in CH-A-561763. The polymer-solubility of the disclosed compounds is, however, inadequate for present requirements.

SUMMARY OF THE INVENTION

The present invention relates to novel colorants for the mass coloring of polymers. In the mass coloring of polar polymers in particular, examples being polyamides, polyesters, polycarbonates and ABS, stringent requirements in terms of their heat stability and light fastness are expected from the dyes used.

The object of the present invention is, therefore, to provide heat-stable, light-fast and readily polymer-soluble colorants.

It has been found that the compounds of the formula (I) defined below surprisingly achieve the stated object.

DESCRIPTION OF THE PREFERRED EMBODIMENTS

The invention provides a compound of the formula (I)

(I)

in which $R_1$ and $R_2$ are identical or different and are hydrogen, $C_1$–$C_6$-alkyl, $C_6$–$C_{10}$-aryl, $(C_6$–$C_{10})$-aryl-$(C_1$–$C_6)$-alkyl or $(C_1$–$C_6)$-alkyl-$(C_6$–$C_{10})$-aryl, it being possible for the alkyl and/or aryl radicals to be substituted by hydroxyl, $C_1$–$C_6$-alkoxy, $C_6$–$C_{10}$-aryloxy or halogen, with the proviso that $R_1$ and $R_2$ are not simultaneously hydrogen, $R_3$ is a radical of the formula (II) or (III)

(II)

in which

Y is sulphur, oxygen or N-$R_4$, in which $R_4$ is hydrogen, $C_1$–$C_6$-alkyl, $C_6$–$C_{10}$-aryl, $(C_6$–$C_{10})$-aryl-$(C_1$–$C_6)$-alkyl or $(C_1$–$C_6)$-alkyl-$(C_6$–$C_{10})$-aryl, it being possible for the alkyl and/or aryl radicals to be substituted by hydroxyl, $C_1$–$C_6$-alkoxy, $C_6$–$C_{10}$-aryloxy or halogen;

(III)

in which
$R_5$ is hydrogen, halogen, $R_6$—O— or $R_6$—S—, in which $R_6$ is $C_1$–$C_6$-alkyl, $C_6$–$C10$-aryl, $(C_6$–$C_{10})$-aryl-$(C_1$–$C_6)$-alkyl or $(C_1$–$C_6)$-alkyl-$(C_6$–$C_{10})$-aryl, in which the alkyl and/or aryl radicals can be substituted by hydroxyl, $C_1$–$C_6$-alkoxy, $C_6$–$C_{10}$-aryloxy or halogen.

Preferred compounds of the formula (I) are those in which $R_1$ and $R_2$ are hydrogen, methyl, ethyl, propyl, phenyl, methylphenyl or methoxyphenyl, subject to the abovementioned proviso.

Compounds of the formula (I) which are also preferred are those in which $R_4$ is hydrogen, methyl, ethyl or phenyl.

Preference is also given to compounds of the formula (I) in which $R_5$ is hydrogen, chlorine, bromine, methoxy, ethoxy, phenoxy, —NH—$C_6H_4$—$OCH_3$, —O—$C_6H_4$—$OCH_3$ or —S—$C_6H_4$—$OCH_3$.

Particular preference is given to compounds of the formula (I) in which $R_1$ is hydrogen and
$R_2$ is methyl, ethyl, phenyl or p-methoxyphenyl.

Particular preference is also given to compounds of the formula (I) in which $R_1$ is methyl and
$R_2$ is methyl, ethyl, phenyl or p-methoxyphenyl.

The present invention also provides a process for preparing the compounds of the formula (I), characterized in that a dicarboxylic acid of the formula (IV)

(IV)

or, preferably, one of its functional derivatives, e.g. the acid anhydride or acid halide, is condensed with a diamine or the salt of a diamine of the formula (V)

(V)

Examples of suitable salts of the diamine of the formula (V) are the chlorohydrate or the sulphate.

Condensation takes place in a molar ratio of (IV):(V) of from 0.9:1.1 to 1.1:0.9.

Condensation can be conducted without solvent in the melt at temperatures, for instance, of between 150° C. and 300° C., preferably up to 250° C., or in an inert solvent at temperatures between 25° C. and 300° C., preferably between 100° and 250° C., in the presence or absence of a catalyst.

Examples of suitable solvents are relatively high-boiling aliphatic or aromatic, substituted or unsubstituted hydrocarbons, examples being xylene (mixture), biphenyl, nitrobenzene, chlorobenzenes, chloronaphthalene, glycol ethers, organic acids and acid amides, especially dimethylformamide or N-methyl-pyrrolidone. If the dicarboxylic acid of the formula (IV) is employed in the form of the free acid it is also possible to use water or a relatively high-boiling alcohol, such as ethylene glycol, as solvent.

Examples of possible catalysts are inorganic or organic acids, such as hydrochloric or sulphuric acid, benzenesulphonic, toluenesulphonic or acetic acid. The salts of organic acids, such as sodium or potassium acetate, are in many cases also suitable as catalysts.

Where $R_1$ and $R_2$ are different from one another the product is normally a mixture of all of the possible regioisomeric compounds. The same applies, mutatis mutandis, if asymmetric radicals $R_3$ are used. Examples 1 and 2 below show, exemplarily, all possible regioisomers. The mixtures prepared in this way need not be resolved and can be supplied as a mixture for use in accordance with the invention.

The compounds of the invention are eminently suitable for the coloring of melts of synthetic polar polymers such as, for example, ABS, polyester, polycarbonate or polyamides. Polyamides are, for example, polycondensation products or addition polymerization products of dicarboxylic acids and diamines, e.g. of adipic acid and hexamethylenediamine, of lactams, e.g. ε-caprolactam, or of aminocarboxylic acids, e.g. ω-aminoundecanoic acid. The polyamide melt mixed with the pigment is brought into its final form by conventional methods—for example, in melt spinning, injection molding, extrusion or film blowing machines.

The novel dyes of the formula (I) are extremely stable to the heat stress which is necessarily part of the coloring of synthetic polyamides, and the substrates mass-colored with them also display excellent fastness properties, especially light fastness. Their high polymer-solubility is particularly noteworthy.

The novel compounds of the formula (I) are also suitable as colorants in electrophotographic toners and developers, such as one- or two-component powder toners (also called one- or two-component developers), magnetic toners, liquid toners, polymerization toners and specialty toners (literature: L. B. Schein, "Electrophotography and Development Physics"; Springer Series in Electrophysics 14, Springer Verlag, 2nd Edition, 1992).

Typical toner binders are addition polymerization, polyaddition and polycondensation resins, such as styrene, styrene-acrylate, styrene-butadiene, acrylate, polyester and phenol-epoxy resins, polysulphones, polyurethanes, individually or in combination, and also polyethylene and polypropylene, which may comprise further constituents, such as charge control agents, waxes or flow assistants, or may be modified subsequently with these additives.

The novel compounds of the formula (I) are suitable, furthermore, as colorants in powders and powder coating materials, especially in triboelectrically or electrokinetically sprayable powder coating materials which are used for the surface coating of articles made, for example, from metal, wood, plastic, glass, ceramic, concrete, textile material, paper or rubber (J. F. Hughes, "Electrostatics Powder Coating" Research Studies, John Wiley & Sons, 1984). metal, wood, plastic, glass, ceramic, concrete, textile material, paper or rubber (J. F. Hughes, "Electrostatics Powder Coating" Research Studies, John Wiley & Sons, 1984).

Powder coating resins that are typically employed are epoxy resins, carboxyl- and hydroxyl-containing polyester resins, polyurethane resins and acrylic resins, together with customary hardeners. Combinations of resins are also used. For example, epoxy resins are frequently employed in combination with carboxyl- and hydroxyl-containing polyester resins. Typical hardener components (as a function of the resin system) are, for example, acid anhydrides, imidazoles and also dicyanodiamide and its derivatives, blocked isocyanates, bisacylurethanes, phenolic and melamine resins, triglycidyl isocyanurates, oxazolines and dicarboxylic acids.

In addition, the novel compounds of the formula (I) are suitable as colorants in ink-jet inks, both aqueous and non-aqueous, and in those inks which operate in accordance with the hot-melt process.

In the examples below, parts are by weight.

EXAMPLE 1

98 parts of 5,6-diamino-1-methyl-2(3H)benzimidazolone are mixed with 108.9 parts of naphthalene-1,8-dicarboxylic anhydride in 1200 parts of dimethylformamide. The suspension is heated under reflux for 3 hours. Then 160 parts of dimethylformamide are added, and water/dimethylformamide is distilled off until the temperature has reached 150° C. After an hour the mixture of the compounds of the formulae (a) and (b)

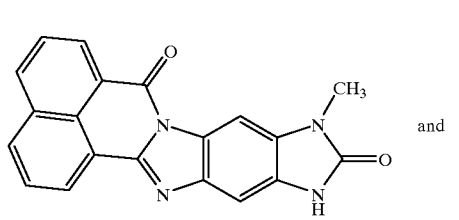

(a)

and

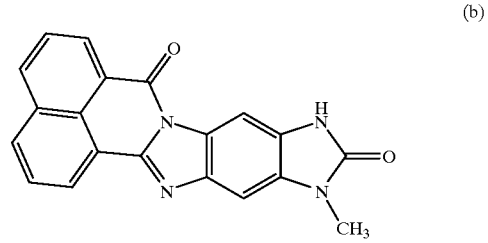

(b)

is filtered at 120° C. and the solid product is washed with hot dimethylformamide and warm water and dried. This gives 167 parts of an orange-colored powder.

EXAMPLE 2

133 parts of benzo[K,l]thioxanthene-3,4-dicarboxylic anhydride are suspended in 1600 parts of N-methylpyrrolidone and 150 parts of acetic acid. At room temperature, 78 parts of 5,6-diamino-1-methyl-2(3H) benzimidazolone are added. The suspension is heated under reflux for 3 hours. After 2 hours, th mixture of the products of the formulae (c), (d), (e) and (f)

(c) 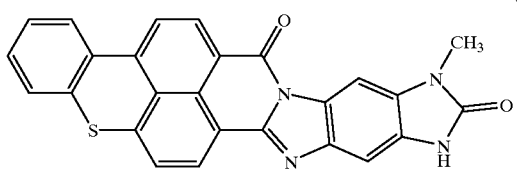
(d) 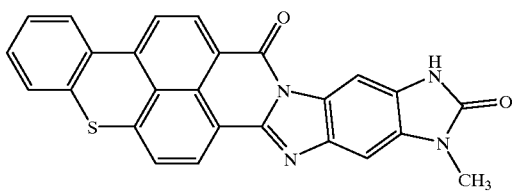
(e) 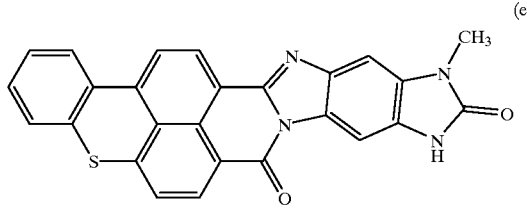
(f) 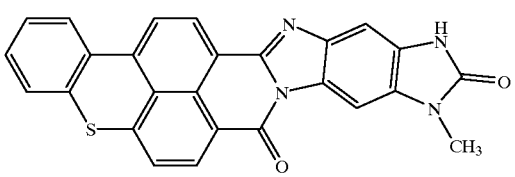
is filtered at 120° C. and the solid product is washed with hot N-methylpyrrolidone and with methanol and dried. This gives 164 parts of a dark red powder.
The dyes listed in Table 1 below are prepared in analogy to Example 2.
TABLE 1
$R_3$ = formula (II)
| Ex. No. | $R_1$ | $R_2$ | $R_3$ | Shade in nylon 6,6 |
|---|---|---|---|---|
| 3 | CH₃ | CH₃ | 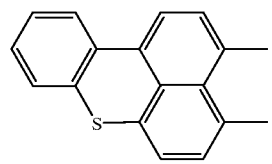 and 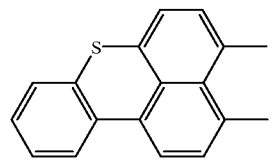 | red |
| 4 | CH₃ | C₂H₅ | " | red |
| 5 | H | C₆H₅ | " | orange-red |
| 6 | H | p-C₆H₄OCH₃ | " | red-violet |
| 7 | H | CH₃ | 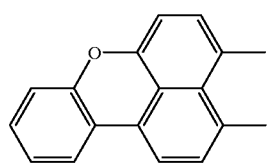 and | orange-red |

TABLE 1-continued
R₃ = formula (II)
| Ex. No. | R₁ | R₂ | R₃ | Shade in nylon 6,6 |
|---|---|---|---|---|
|  |  |  | 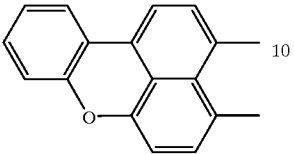 |  |
| 8 | CH₃ | CH₃ | " | orange-red |
| 9 | H | C₂H₅ | " | orange |
| 10 | H | C₆H₅ | " | orange |
| 11 | H | CH₃ | 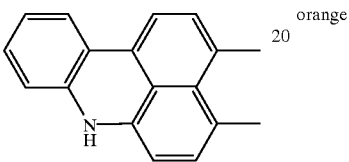 and 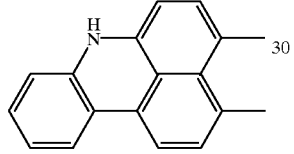 | orange |
| 12 | CH₃ | CH₃ | " | orange |
| 13 | H | C₂H₅ | " | orange |
| 14 | H | C₆H₅ | " | orange |
| 15 | H | CH₃ | 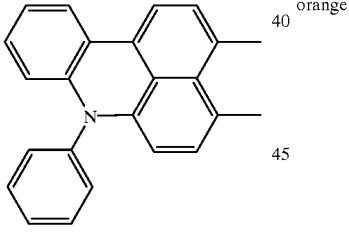 and 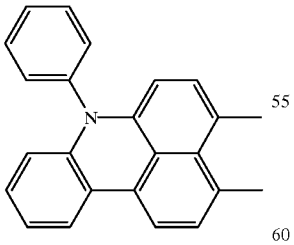 | orange |
| 16 | CH₃ | CH₃ | " | orange |
| 17 | H | C₂H₅ | " | orange |
| 18 | H | C₆H₅ | " | orange |
| 19 | H | p-C₆H₄OCH₃ | " | orange-red |

The dyes listed in Table 2 below are prepared in analogy to Example 1.
TABLE 2
$R_3$ = formula (III)
| Ex. No. | $R_1$ | $R_2$ | $R_3$ | Shade in nylon 6,6 |
|---|---|---|---|---|
| 20 | H | $C_2H_5$ | 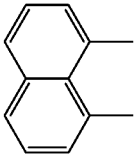 | yellow |
| 21 | H | $C_6H_5$ | " | greenish yellow |
| 22 | H | p-$C_6H_4OCH_3$ | " | orange |
| 23 | $CH_3$ | $C_2H_5$ | " | yellow |
| 24 | H | $CH_3$ | 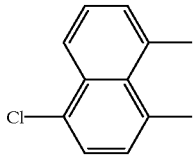 and 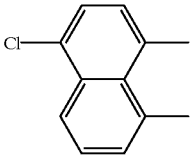 | yellow |
| 25 | H | $C_2H_5$ | " | yellow |
| 26 | $CH_3$ | $C_2H_5$ | " | yellow |
| 27 | H | $CH_3$ | 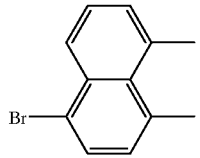 and 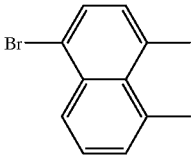 | yellow-orange |
| 28 | H | $C_2H_5$ | " | yellow-orange |
| 29 | $CH_3$ | $C_2H_5$ | " | yellow |
| 30 | H | $CH_3$ | 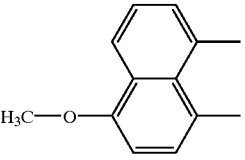 and | orange |

TABLE 2-continued

R₃ = formula (III)

| Ex. No. | R₁ | R₂ | R₃ | Shade in nylon 6,6 |
|---|---|---|---|---|
| | | | 4-methoxy-5,8-dimethylnaphthyl | |
| 31 | H | C₂H₅ | " | orange |
| 32 | CH₃ | C₂H₅ | " | orange |
| 33 | H | CH₃ | 4-phenoxy-5,8-dimethylnaphthyl and 4-phenoxy-5,8-dimethylnaphthyl (isomer) | orange-red |
| 34 | H | C₂H₅ | " | orange-red |
| 35 | CH₃ | C₂H₅ | " | orange-red |
| 36 | H | CH₃ | 4-(4-methoxyphenylamino)-5,8-dimethylnaphthyl and isomer | red |
| 37 | H | C₂H₅ | " | red |
| 38 | CH₃ | C₆H₅ | " | yellow-orange |

TABLE 2-continued

R₃ = formula (III)

| Ex. No. | R₁ | R₂ | R₃ | Shade in nylon 6,6 |
|---|---|---|---|---|
| 39 | H | CH₃ | 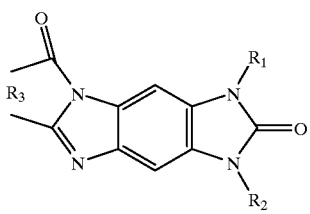 and | red |
| 40 | H | C₂H₅ | " | red |
| 41 | CH₃ | C₆H₅ | " | red |

USE EXAMPLE 100 parts of polycaprolactam in the form of a powder are mixed with 0.1 and with 1.0 part respectively of the dye from Example 1 in powder form in a drum mixer. After a short time, the powder is uniformaly distributed and adheres to the granules. After about 10 minutes, the mixture is dried at 120° C. for 16 hours, transferred to a melt spinning machine and following a residence time of about 8 minutes is spun to fibers at 275–280° C. under a nitrogen atmosphere. The yellow-colored fibers are extremely lightfast.

All other known synthetic polyamids (nylon, Perlon, etc.) can be mass-colored in the same way, as can polyesters, ABS and polycarbonates, using the compounds of examples 1 to 41.

We claim:

1. A compound of the formula (I)

(I)

[structure of compound I]

in which

R₁ and R₂ are identical or different and are hydrogen, $C_1$–$C_6$-alkyl, $C_6$–$C_{10}$-aryl, ($C_6$–$C_{10}$)-aryl-($C_1$–$C_6$)-alkyl or ($C_1$–$C_6$)-alkyl-($C_6$–$C_{10}$)-aryl, optionally substituted by hydroxyl, $C_1$–$C_6$-alkoxy, $C_6$–$C_{10}$-aryloxy or halogen, with the proviso that R₁ and R₂ are not simultaneously hydrogen, R₃ is a radical of the formula (II) or (III)

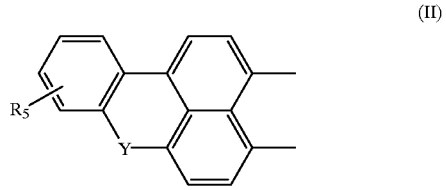

(II)

in which

Y is sulphur, oxygen or N—R₄, in which R₄ is hydrogen, $C_1$–$C_6$-alkyl, $C_6$–$C_{10}$-aryl, ($C_6$–$C_{10}$)-aryl-($C_1$–$C_6$)-alkyl or ($C_1$–$C_6$)-alkyl-($C_6$–$C_{10}$)-aryl, optionally substituted by hydroxyl, $C_1$–$C_6$-alkoxy, $C_6$–$C_{10}$-aryloxy or halogen;

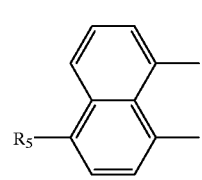

(III)

in which $R_5$ is hydrogen, halogen,

$R_6$—O— or $R_6$—S—, in which $R_6$ is $C_1$–$C_6$-alkyl, $C_6$–$C_{10}$-aryl, $(C_6$–$C_{10})$-aryl-$(C_1$–$C_6)$-alkyl or $(C_1$–$C_6)$-alkyl-$(C_6$–$C_{10})$-aryl, in which the alkyl and/or aryl radicals can be substituted by hydroxyl, $C_1$–$C_6$-alkoxy, $C_6$–$C_{10}$-aryloxy or halogen.

2. A compound according to claim 1, wherein
$R_1$ and $R_2$ are hydrogen, methyl, ethyl, propyl, phenyl, methylphenyl or methoxyphenyl.

3. A compound according to claim 1, wherein
$R_4$ is hydrogen, methyl, ethyl or phenyl.

4. A compound according to claim 1, wherein
$R_5$ is hydrogen, chlorine, bromine, methoxy, ethoxy, phenoxy, —NH—$C_6H_4$—$OCH_3$, —O—$C_6H_4$—$OCH_3$ or —S—$C_6H_4$—$OCH_3$.

5. A compound according to claim 1, wherein
$R_1$ is hydrogen and
$R_2$ is methyl, ethyl, phenyl or p-methoxyphenyl.

6. A compound according to claim 1, wherein
$R_1$ is methyl and
$R_2$ is methyl, ethyl, phenyl or p-methoxyphenyl.

7. A process for preparing a compound of the formula (I)

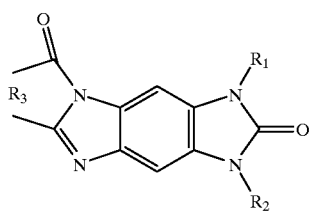

(I)

in which
$R_1$ and $R_2$ are identical or different and are hydrogen, $C_1$–$C_6$-alkyl, $C_6$–$C_{10}$-aryl, $(C_6$–$C_{10})$-aryl-$(C_1$–$C_6)$-alkyl or $(C_1$–$C_6)$-alkyl-$(C_6$–$C_{10})$-aryl, optionally substituted by hydroxyl, $C_1$–$C_6$-alkoxy, $C_6$–$C_{10}$-aryloxy or halogen,
with the proviso that $R_1$ and $R_2$ are not simultaneously hydrogen,
$R_3$ is a radical of the formula (II) or (III)

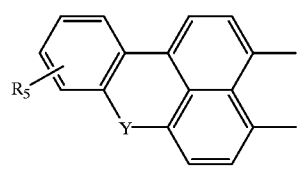

(II)

in which
Y is sulphur, oxygen or N—$R_4$, in which $R_4$ is hydrogen, $C_1$–$C_6$-alkyl, $C_6$–$C_{10}$-aryl, $(C_6$–$C_{10})$-aryl-$(C_1$–$C_6)$-alkyl or $(C_1$–$C_6)$-alkyl-$(C_6$–$C_{10})$-aryl, optionally substituted by hydroxyl, $C_1$–$C_6$-alkoxy, $C_6$–$C_{10}$-aryloxy or halogen;

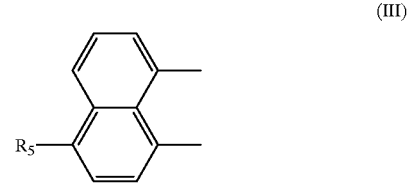

(III)

in which
$R_5$ is hydrogen, halogen,

$R^6$—O— or $R_6$—S—, in which $R_6$ is $C_1$–$C_6$-alkyl, $C_6$–$C_{10}$-aryl, $(C_6$–$C_{10})$-aryl-$(C_1$–$C_6)$-alkyl or $(C_1$–$C_6)$-alkyl-$(C_6$–$C_{10})$-aryl, in which the alkyl and/or aryl radicals may be substituted by hydroxyl, $C_1$–$C_6$-alkoxy, $C_6$–$C_{10}$-aryloxy or halogen
wherein a dicarboxylic acid of the formula (IV)

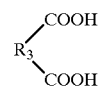

(IV)

in which $R_3$ is defined as above,
or one of its functional derivatives is condensed with a diamine or the salt of a diamine of the formula (V)

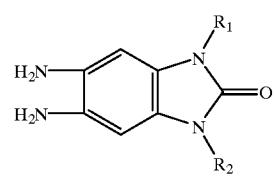

(V)

in which $R_1$ and $R_2$ are defined as above.

8. A process according to claim 7, wherein the functional derivative of the dicarboxylic acid is the acid anhydride or acid chloride.

9. A method for coloring synthetic polyamides, polyesters, ABS or polycarbonates, for coloring electrophotographic toners and developers, powder coating materials, and ink-jet inks, by applying thereto or incorporating therein a compound according to claim 1.

10. Method according to claim 9 for mass-coloring polycondensates of dicarboxylic acids and diamines, of lactams or of aminocarboxylic acids.

* * * * *